United States Patent [19]

Morez

[11] Patent Number: 4,895,149

[45] Date of Patent: Jan. 23, 1990

[54] APPARATUS FOR NON-INVASIVE STIMULATION OF ACUPUNCTURE POINTS

[76] Inventor: Jean-Bernard Morez, 6 bis Place de l'Europe, 59240 Dunkerque, France

[21] Appl. No.: 644,683

[22] Filed: Aug. 27, 1984

[30] Foreign Application Priority Data

Aug. 29, 1983 [FR] France ............................... 83 14020

[51] Int. Cl.[4] ............................................... A61N 1/00

[52] U.S. Cl. ................................ 128/419 R; 128/421; 128/907

[58] Field of Search ............... 128/421, 422, 907, 746, 128/735, 419 R, 395; 179/107 FD

[56] References Cited

U.S. PATENT DOCUMENTS 4,232,678 11/1980 Skovajsa ............................ 128/395
4,267,838 5/1981 McCall ............................... 128/907
4,450,846 5/1984 McCall ............................... 128/907

FOREIGN PATENT DOCUMENTS 2445152 7/1980 France .
2445153 7/1980 France .

*Primary Examiner*—Max Hindenburg
*Assistant Examiner*—J. P. Lacyk
*Attorney, Agent, or Firm*—Kerkam, Stowell, Kondracki & Clarke

[57] ABSTRACT

Apparatus for non-invasive stimulation of the points commonly called acupuncture points on the cutaneous surface of the body is characterized in that it includes means for generating five primary sound frequencies which, instead of corresponding to the fundamental frequencies of the five notes of the early musical scale at which particular body organs resonate, are harmonic frequencies of these mean fundamental frequencies obtained by adopting for each of them a harmonic of an order chosen so as to organize the mean harmonic frequencies in such a manner that in passing from the highest to the lowest, the cycle of the five elements of nature is transversed and the body organs are treated in accordance with the law of generation.

15 Claims, 2 Drawing Sheets

Fig:_3
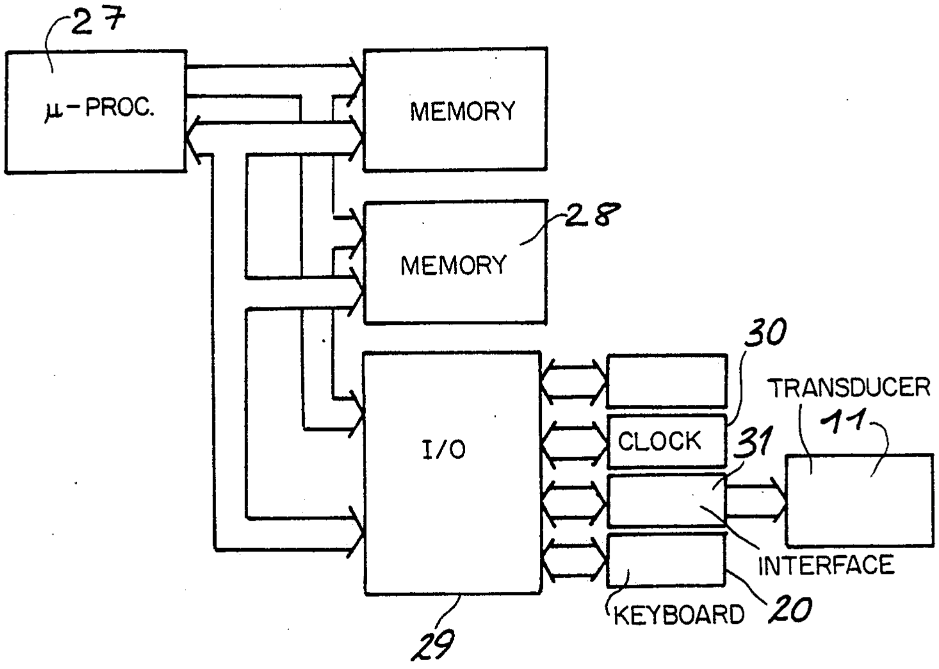
Fig:_4
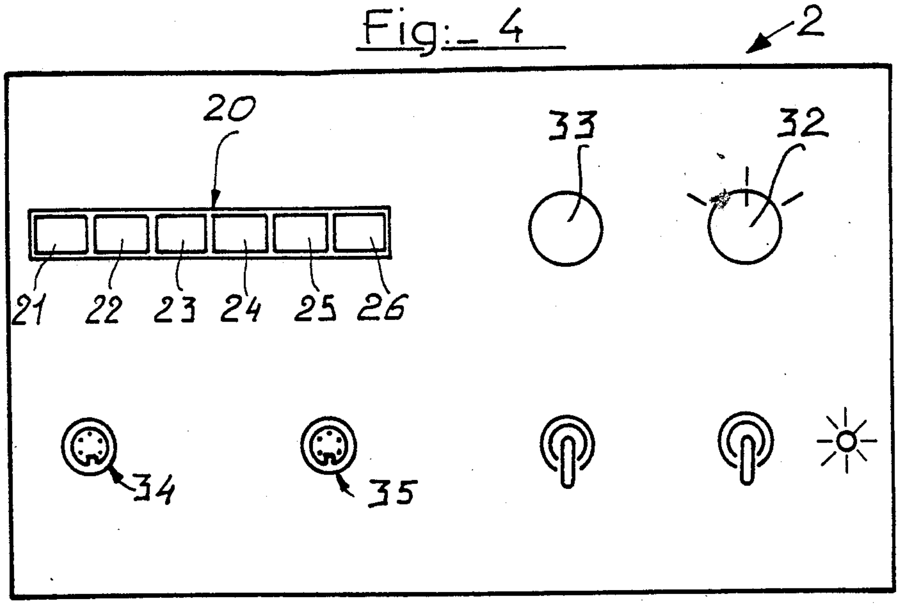

APPARATUS FOR NON-INVASIVE STIMULATION OF ACUPUNCTURE POINTS

FIELD OF THE INVENTION

The invention relates to a novel apparatus for the non-invasive stimulation of points, commonly known as acupuncture points, on the cutaneous surface of the body.

BACKGROUND OF THE INVENTION

It is known (NEI KING, chapter 10, paragraph 65) that the five notes of the earliest musical scale have a correspondence with the five elements of nature and with the five viscera, and are interrelated in a substantially constant ratio.

In classifying the elements according to the law of generation, it is known that:

- the note known as "JIAO", which is related to the others in a ratio of approximately 64, corresponds to wood and to the liver;
- the note "ZHI", which is related to the others in a ratio of approximately 54, corresponds to fire and to the heart;
- the note "GONG", which is related to the others in a ratio of 81, corresponds to the earth and to the spleen;
- the note "SHANG", which is related to the others in a ratio of 72, corresponds to metal and to the lungs; and
- the note "YU", which is related to the others in a ratio of 48, corresponds to water and to the kidneys.

These ratios are also confirmed in the "Tetractys pythagoricienne" with the fifth, the fourth and the octave intervals in the dodecaphonic or usual modern musical scale.

Based on ratios approximately defining sound wave frequencies, each of them may be expressed as a mean number of complete cycles per second, or in other words as a mean Hertz frequency.

Furthermore, various apparatus for non-invasive stimulation of acupuncture points utilizing waves in accordance with the frequencies is also known.

Certain ones of such apparatus (French Patents 2.371.935 and 2.498.927) utilize either a value (75 Hz) which approximates the mean frequency (72 Hz) of the note "SHANG", or integral multiples of this value, but this is done not to express a sound wave representing the information furnished at the acupuncture points, but to define the quenching frequency of a light wave generally in the infrared zone of the spectrum by an electroluminous diode.

These type of apparatus principally act, more or less superficially, upon the energies of maintenance, that is, on the trophic and defense energies, but also, accessorily, on the "informative" aspect of the psycho-informative energy.

These apparatuses, which have only a superficial and transient effect on the clinical level, thus are furthermore not adapted to act on the energy of programming-/regulation.

These various apparatuses thus have made predominant use of one of the frequencies defined in the classical texts, and hence are incomplete and not long-lasting in effect.

Hence at the present time, there is nothing available for complete constitutional action, contributing to reinserting a patient into time and space, except the traditional needles, with the disadvantages they have, both because of the fear they evoke, especially in the youngest patients, and because of the risks of infection due to the perforation of the skin.

One result the invention seeks to obtain is an apparatus the action of which is constitutional and durable and which offers the advantages of the five mean frequencies mentioned above.

To take into account the particular characteristics of the patients, it must furthermore be readily possible to furnish these waves not merely at exactly the mean value of the frequency of each note, but also at a frequency slightly different from that. A further result the invention seeks to obtain is an apparatus having a range of control of plus or minus four Hz with respect to each mean frequency.

An apparatus emitting sound waves at the five mean frequencies mentioned above and with the control range mentioned above will not be suitable, however, because first, certain control ranges can thus overlap or cross over one another in an undesirable manner, and so the passage of one wave to another upward or downward in the order of their frequencies causes wandering among the five elements in a disordered manner in terms of the law of generation.

Furthermore, such a wave would have limited penetration and thus would not have a lasting effect.

One result the invention seeks to obtain is an apparatus which, while furnishing the frequencies in an ordered manner, does not produce undesirable overlapping or crossovers in the control ranges.

OBJECT AND SUMMARY OF THE INVENTION

To this end, the object of the invention is an apparatus of the general type described above, in particular characterized in that it includes means for generating five primary sound frequencies which, instead of corresponding to the frequencies known as fundamentals of the five notes mentioned above, are harmonic frequencies of these mean fundamental frequencies obtained by adopting for each of them a harmonic of an order chosen so as to organize the mean harmonic frequencies in such a manner that in passing from the highest to the lowest, in seriatum the cycle of the five elements in accordance with the law of generation is traversed.

The invention will be better understood from the ensuing description of a non-limiting exemplary embodiment, taken in conjunction with the drawings.

BRIEF DESCRIPTION OF THE DRAWINGS

FIGS. 3 and 4 show exemplary embodiments for the essential elements of the apparatus.

DESCRIPTION OF THE PREFERRED EMBODIMENT

Figure 1:
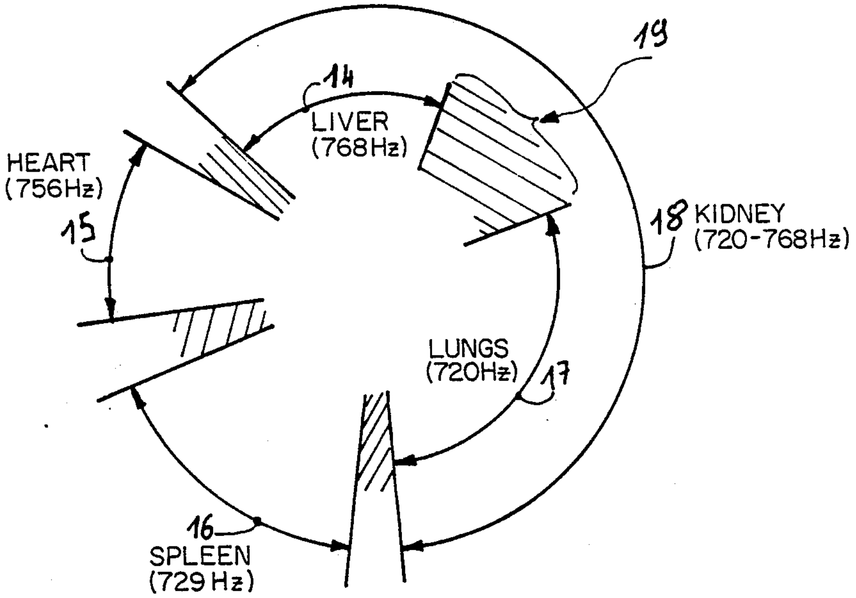
FIG. 1 shows the disposition of the frequencies adopted for the apparatus.
Figure 2:
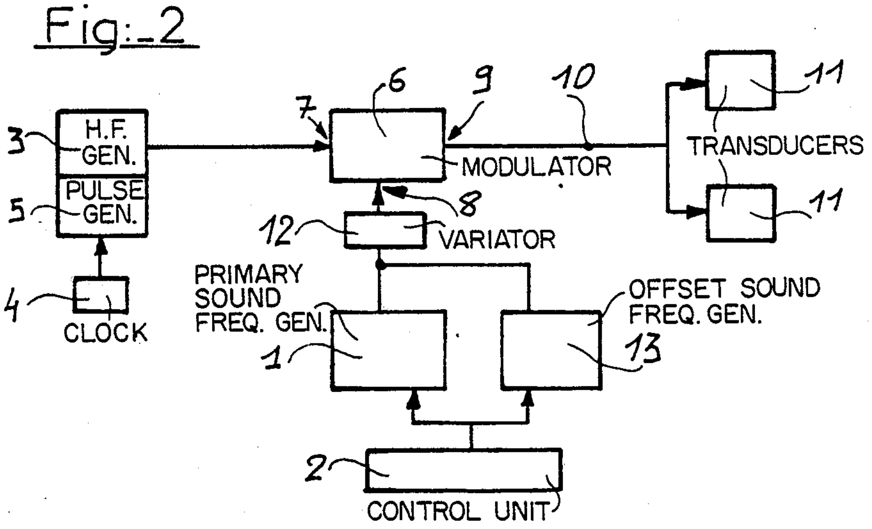
FIG. 2 shows a block diagram of the apparatus.

Taking as the point of departure the finding that the organs resonate in the same manner with harmonic frequencies as with the fundamental frequencies, the apparatus according to one characteristic of the apparatus includes means for generating five primary sound frequencies which, instead of corresponding to the frequencies known as fundamentals of the five notes mentioned above, are harmonic frequencies of these mean fundamental frequencies obtained by adopting for each of them a harmonic number or order which is chosen so as to organize the mean harmonic frequencies in such a manner that in passing from the highest to the lowest, the cycle of the five elements in accordance with the law of generation is traversed.

In an advantageous manner, these harmonic frequencies will be the following:

a harmonic frequency of order 12X for the fundamental frequency of 64 Hz to which wood and the liver correspond, where X is an integer. Assuming X=1, 12X means the 12th harmonic, which for 64 Hz corresponds to a mean harmonic frequency of 768 Hz;

a harmonic frequency of order 14X for the fundamental frequency of 54 Hz, to which fire and the heart correspond, and which, assuming X=1, is a mean harmonic frequency of 756 Hz;

a harmonic frequency of order 9X for the fundamental frequency of 81 Hz, to which earth and the spleen correspond, and which, assuming X=1, is a mean harmonic frequency of 729 Hz;

a harmonic frequency of order 10X for the fundamental frequency of 72 Hz, to which metal and the lungs correspond, and which, assuming X=1, is a mean harmonic frequency of 720 Hz;

harmonic frequencies of order 15X and 16X for the fundamental frequency of 48 Hz, to which water and the kidney correspond, and which, assuming X=1, is a mean harmonic frequency of 720 and 768 Hz, respectively, such as to correspond advantageously to the more and less elevated mean harmonic frequencies and serves to obtain an overriding action upon the zone located between the kidney and the liver.

In all cases, X obviously remains an integer at least equal to 1.

The means generating the five primary sound frequencies may be any known generator 1 placed under the control of a control unit 2 for controlling the frequency furnished by the generator 1 and which, whether the control is specialized or general, thus controls the scanning or sweep of the frequencies.

Given that the corresponding sound waves would have little penetration and thus a very brief effect, regardless of the means 1 and 2 above, the apparatus includes a generator 3 of a much higher frequency, for instance 1 MHz, and an internal clock 4 for controlling the constancy of this frequency, as well as a pulse generator means 5 for slicing this frequency into a train of pulses, each of which has a duration of one-tenth of a period The apparatus also includes a modulator 6 of this high frequency, perhaps sliced into pulses, which reaches one (7) of its inputs 7, 8, which modulation is effected via the particular harmonic frequency emitted by the generator 1 mentioned above.

Connected to the output 9 of the modulator 6 is a line 10 for supplying the high frequency, then modulated, to at least one transducer 11, which, being placed facing the selected acupuncture points, assures the intended action.

These transducer 11 may be of any known type; they will of course be adapted to the high frequency selected.

For example, if this high frequency is ultrasonic, it may involve piezoceramic cells, and if the frequency is in the range of light, it may involve electroluminous diodes or a laser diode with the light wave being transmitted directly or indirectly, for example with the aid of optical fibers.

At the outlet of the generator 1 of primary sound frequencies, a variator 12 enables the variation of the signal level over time, for example in a ratio of from zero to 30% higher or lower.

Parallel to this primary sound frequency generator 1, the apparatus may include a second generator 13 of offset sound frequencies which as compared with the primary frequencies are different by a slight amount, for example 6 Hz, which creates a beat equivalent to this difference.

As shown in FIG. 1, with the musical scales and frequency ranges thus obtained, the frequency ranges 14, 15, 16, 17, respectively, of the liver, the heart, the spleen and the lungs, do not overlap or cross over one another, and at the interior of these organs, the frequencies remain close to the mean frequency. (For X=1, the mean frequency of each range is shown on the figure.)

Only the range of the kidney 18 intentionally overlaps the ranges of the liver and the lungs, passing via a transition zone 19 corresponding to the prenatal period.

This apparatus will act principally on the energy of programming/regulation and this is the source of all its originality and its usefulness in therapy.

It will also act upon the psycho-informative energy, essentially in its temperamental aspect.

This does not mean that the ultrasounds modulated by a sound frequency will not have any effect upon the energies of maintenance, but rather that they will have only an indirect effect on them, varying over time, which on the clinical level will prove to be more durable than the effect that would have been obtained with a more specific stimulation of the energies of maintenance.

As mentioned above, each acupuncture point may thus be stimulated either by a single frequency or by a sweep of frequencies which in the above-mentioned example lasts approximately 30 seconds for one complete sweep cycle.

To this end, the control unit 2 (FIG. 4) includes a keyboard 20 provided with keys 21–25 for each organ and one key 26 determining a sweep of the frequencies.

The key 25 relating to the kidney alternates the two corresponding harmonic frequencies, for example every five seconds.

Based on the above information, one skilled in the art will be able to realize the apparatus without performing work on the level of invention.

Various embodiments are possible, for example in the form of a hard wired logic assembly, or by analog electronic concepts.

Preferably the apparatus will be designed around a central unit 27 comprising a microprocessor monitored by a clock, so that the frequencies emitted will have a precision which at worst is on the order of one Hz.

The various sound frequencies, their cyclical ratios, and the beat frequencies are programmed in a memory 28 of the EPROM type.

An input and output circuit 29 will permit the data arriving from the exterior to be put through to the microprocessor 27, the keyboard 20, for example, or the clock 30, as far as the inputs are concerned.

It will in exchange furnish the data originating in the microprocessor 27 to the transducer 11, passing via the interface 31.

For instance, it it is desired that the frequency corresponding to the heart be used, the 756 Hz key of the keyboard is pressed, the central unit generates signals corresponding to the instructions furnished by the input/output assembly, as well as by the memory 28, by way of the interface 31; these signals are applied with the aid of the transducer 11 to the selected acupuncture points.

The apparatus may also be provided with a means 32 for regulating power, such as a switch with a plurality of positions.

It may also include an amplifier 33, enabling the auditive materialization of the frequencies.

The two outputs 34, 35 enable the use of two transistors, with a view to joint usage.

Advantageously, two apparatuses of the type described above will be used jointly at the time of treatment, of course for the sake of increasing the efficacy of the desired stimulation.

I claim:

1. Apparatus for non-invasive stimulation of acupuncture points on a cutaneous surface of a human body comprising sound frequency generating means for generating five primary sound frequencies, each of which is a different higher order harmonic of one of five fundamental sound frequencies which are effective for treating different organs of the body, said five fundamental sound frequencies and the organs treated thereby, arranged in a predetermined order, being, approximately, 64 Hz corresponding to a liver, 54 Hz corresponding to a heart, 81 Hz corresponding to a spleen, 72 Hz corresponding to lungs, and 48 Hz corresponding to a kidney; transducer means for applying the primary sound frequencies to an acupuncture point on the body for treating the organs; and control means for controlling the sound frequency generating means such that the five primary sound frequencies are generated in seriatum in order of decreasing frequency, and wherein the different harmonic orders of the five primary sound frequencies are selected such that when the primary sound frequencies are applied in order of decreasing frequency the organs are treated in said predetermined order.

2. The apparatus of claim 1, wherein said primary sound frequencies comprise a first primary frequency having a harmonic order of 12X times the fundamental sound frequency of 64 Hz, a second primary frequency having a harmonic order of 14X times the fundamental sound frequency of 54 Hz, a third primary frequency having a harmonic order of 9X times the fundamental sound frequency of 81 Hz, a fourth primary frequency having a harmonic order of 10X times the fundamental sound frequency of 72 Hz, and a fifth primary frequency having a harmonic order of either 15X or 16X times the fundamental sound frequency of 48 Hz, wherein X is an integer at least equal to 1.

3. The apparatus of claim 1, wherein said five primary sound frequencies comprise a first primary sound frequency of the order of 768 Hz, a second primary sound frequency of the order of 756 Hz, a third primary sound frequency of the order of 729 Hz, a fourth primary sound frequency of the order of 720 Hz, and a fifth primary sound frequency of the order of either 720 or 768 Hz.

4. The apparatus of claim 1, further comprising a high frequency generator for producing a high-frequency carrier signal, and means for modulating the high-frequency carrier signal with said five primary sound frequencies, the modulated high-frequency carrier being applied to said transducer means.

5. The apparatus of claim 4, further comprising means for converting the high-frequency carrier signal into a train of pulses prior to said modulating means.

6. The apparatus of claim 5, wherein said converting means includes means for converting the high-frequency carrier into pulses having a duration of the order of one-tenth of a period of the frequency of the carrier signal.

7. The apparatus of claim 1, wherein said high-frequency is of the order of 1 MHz.

8. The apparatus of claim 1 further comprising variator means for varying the output levels of the primary sound frequencies from said generating means.

9. The apparatus of claim 1, wherein said sound frequency generating means comprises means for generating five additional primary sound frequencies which are related to said first-mentioned five primary sound frequencies but which differ in frequency therefrom by a small amount, and means for combining related ones of said first- and second-mentioned five primary sound frequencies so as to produce a beat frequency corresponding to said small amount of frequency difference.

10. The apparatus of claim 1, wherein said transducer means comprises first and second transducers connected in parallel such that said primary sound frequencies may be applied simultaneously to spaced acupuncture points on the body.

11. The apparatus of claim 1, wherein said sound frequency generating means and said control means comprise a microprocessor connected to a memory and to an input and output circuit, said transducer means being interfaced to said input and output circuit, and wherein said memory is programmed with data corresponding to said primary sound frequencies such that upon reading of said data from the memory the primary sound frequencies are produced at said input and output circuit.

12. Apparatus for non-invasive stimulation of acupuncture points on a cutaneous surface of a body comprising sound frequency generating means for generating five primary frequencies, each of which is a different higher order harmonic of one of five fundamental sound frequencies, the five fundamental sound frequencies being arranged in a set in a predetermined order of frequencies, said predetermined order being frequencies of approximately 64 Hz, 54 Hz, 81 Hz, 72 Hz and 48 Hz; transducer transducer means for applying the primary sound frequencies to an acupuncture point on the body; and control means for controlling the sound frequency generating means such that the five primary sound frequencies are generated in seriatum in accordance with decreasing frequency, and wherein the different harmonic orders of the five primary sound frequencies are selected such that when the five primary sound frequencies are arranged in order of decreasing frequency the resulting order corresponds to said predetermined order of the five fundamental sound frequencies.

13. The apparatus of claim 12, wherein said five primary sound frequencies comprise a first primary sound frequency which is the twelfth harmonic of 64 Hz, a second primary sound frequency which is the fourteenth harmonic of 54 Hz, a third primary sound frequency which is the ninth harmonic of 81 Hz, a fourth primary sound frequency which is the tenth harmonic of 72 Hz, and a fifth primary sound frequency which is the fifteenth or sixteenth harmonic of 48 Hz.

14. A method of non-invasive stimulation of acupuncture points on a cutaneous surface of a human body comprising generating five primary sound frequencies, each of which is a different higher order harmonic of one of five fundamental sound frequencies which are effective for treating corresponding different organs of the body, said five fundamental sound frequencies and said corresponding organs, arranged in a predetermined order, being approximately 64 Hz corresponding to a liver, approximately 54 Hz corresponding to a heart, approximately 81 Hz corresponding to a spleen, approximately 72 Hz corresponding to lungs, and approximately 48 Hz corresponding to a kidney; applying the five primary sound frequencies to an acupuncture point on the body; and controlling said applying such that the five primary sound frequencies are applied in seriatum in order of decreasing frequency, and wherein the different harmonic orders of the five primary sound frequencies are selected such that when applied in seriatum in order of decreasing frequency, the organs are treated in accordance with said predetermined order.

15. The method of claim 14, wherein the harmonic orders of the primary sound frequencies are selected such that a first primary sound frequency is of the order of 12X times the fundamental sound frequency of 64 Hz, a second primary sound frequency is of the order of 14X times the fundamental sound frequency of 54 Hz, a third primary sound frequency is of the order of 9X times the fundamental sound frequency of 81 Hz, a fourth primary sound frequency is of the order of 10X times the fundamental sound frequency of 72 Hz, and the fifth primary sound frequency is of the order of 15X or 16X times the fundamental sound frequency of 48 Hz, where X is an integer at least equal to one.

* * * * *

UNITED STATES PATENT AND TRADEMARK OFFICE

CERTIFICATE OF CORRECTION

PATENT NO. : 4,895,149

DATED : January 23, 1990

INVENTOR(S) : Jean-Bernard Morez

It is certified that error appears in the above-identified patent and that said Letters Patent is hereby corrected as shown below:

Col. 6, line 47, (claim 12, line 10) delete "transducer at the second ocurrence.

Signed and Sealed this

Eleventh Day of February, 1992

*Attest:*

HARRY F. MANBECK, JR.

*Attesting Officer* *Commissioner of Patents and Trademarks*